United States Patent [19]

Warriner

[11] Patent Number: Plant 7,582

[45] Date of Patent: Jul. 9, 1991

[54] ROSE PLANT JACOH

[75] Inventor: William A. Warriner, Tustin, Calif.

[73] Assignee: Bear Creek Gardens, Inc., Medford, Oreg.

[21] Appl. No.: 490,841

[22] Filed: Mar. 8, 1990

[51] Int. Cl.[5] ..... A01H 5/00

[52] U.S. Cl. ..... Plt./12

[58] Field of Search ..... Plt./12,16

*Primary Examiner*—James R. Feyrer

*Attorney, Agent, or Firm*—Klarquist, Sparkman, Campbell, Leigh and Whinston

[57] ABSTRACT

A hybrid tea rose variety having bright orange color with distinctive lighter reverse, heavy petal substance, strong upright growth, resistance to powdery mildew, and large flower when fully open.

1 Drawing Sheet

1

This present invention relates to a new and distinct variety of rose plant named Jacoh of the hybrid tea class which was originated by me by crossing the variety Prominent, U.S. Plant Pat. No. 3,380, with an unnamed seedling.

The primary objective of this breeding was to produce a new rose variety having the bright orange color and disease tolerance of Prominent with the large flower of the unnamed seedling. The objective was substantially achieved along with other desirable improvements as evidenced by the following unique combination of characteristics which are outstanding in the new variety and which distinguish it from its parents as well as from all other varieties of which I am aware:

1. Bright orange color with distinctive lighter reverse.
2. Heavy petal substance.
3. Strong upright growth.
4. Resistance to powdery mildew.
5. Large flower when fully open.

Asexual reproduction of the new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Prominent, U.S. Plant Pat. No. 3,380.

*Pollen parent.*—An unnamed seedling.

Classification:

*Botanical.*—*Rosa hybrida.*

*Commercial.*—Hybrid tea.

2

FLOWER

Observations made June to October from specimens grown in a garden in Somis, Calif.

Bloom habit: Recurrent.

Bud:

*Size.*—1¾ inch when the petals start to unfurl.

*Form.*—Short, pointed ovoid.

*Color.*—When sepals first divide: Orange-red Group 32A. When half blown: The upper sides of the petals are Orange-red Group 33B; and the lower sides of the petals are much lighter beginning at the petal edge with Orange-red 32A and becoming lighter to near 32D near the petal base.

*Sepals.*—Color: Green Group 132B. Surface texture: Covered in fine hairs. Three lightly appendaged sepals and two unappendaged sepals with hairy edges.

*Receptacle.*—Color: Green Group 137D. Shape: Funnel. Size: Medium. Surface: Smooth.

*Peduncle.*—Length: Medium. Surface: Smooth. Color: Medium green. Strength: Stiff.

Bloom:

*Size.*—Large. Average open size is 4½ inches.

*Borne.*—Singly.

*Stems.*—Medium.

*Form.*—When first open: High centered. Permanence: Retains its form to the end, outer petal edges curl back.

*Petalage.*—Number of petals under normal conditions: 25 to 30.

*Color.*—Upper side of petals is: Red-orange Group 32A to B. Reverse side of petals is: Red-orange Group 32A fading top to bottom to 32D. Base of petals is: Yellow half moon at the point of attachment. Major color on the upper side is: Red-orange Group 32A to B.

*Variegations.*—None.

*Discoloration.*—General tonality at end of first day: No change; at the end of the third day: Some petal fading under bright California conditions to Red-orange Group 32B to C.

*Fragrance.*—Slight.

Petals:

*Texture.*—Thick.

*Shape.*—Oval.

*Form.*—Tips slightly recurved.

*Arrangement.*—Imbricated.

*Persistence.*—Drop off cleanly.
*Lastingness.*—On the plant: Long. As a cut flower: Long.

Reproductive parts:
*Anthers.*—Size: Medium. Quantity: Many. Color: Yellow. Arrangement: Regular around styles.
*Filaments.*—Color: White.
*Pollen.*—Color: Gold yellow.
*Styles.*—Color: Yellow.
*Stigmas.*—Color: Greenish white.

Form: Bush.

Growth: Vigorous, upright.

Foliage:
*Number of leaflets on normal mid-stem leaves.*—5.
*Size.*—Medium.
*Quantity.*—Normal.
*Color.*—New foliage: Reddish. Old foliage: Dark green.

Leaflets:
*Shape.*—Oval.
*Texture.*—Leathery.
*Edge.*—Serrated.
*Serration.*—Single, small.
*Petiole.*—Rachis: Green. Underside: Smooth.
*Stipules.*—Short, bearded.

*Disease resistance.*—Resistant to powdery mildew under normal growing conditions at Somis, Calif.

Wood:
*New wood.*—Color: Reddish. Bark: Smooth.
*Old wood.*—Color: Green. Bark: Smooth.

Prickles:
*Quantity.* On main canes from base: Ordinary. On laterals from main canes: Ordinary.
*Form.*—Medium, hooked slightly downward.
*Color when young.*—Red.

Small prickles:
*Quantity.*—On main stalks: Few. On laterals: Few.
*Color.*—Green.

I claim:

1. A new and distinct variety of rose plant of the hybrid tea class, substantially as herein shown and described, characterized particularly as to novelty by its large orange flower coupled with distinctive lighter shade on reverse side of petal, upright vigorous habit of growth, resistance to powdery mildew, heavy petal substance and resistance to powdery mildew under Somis, Calif. conditions.

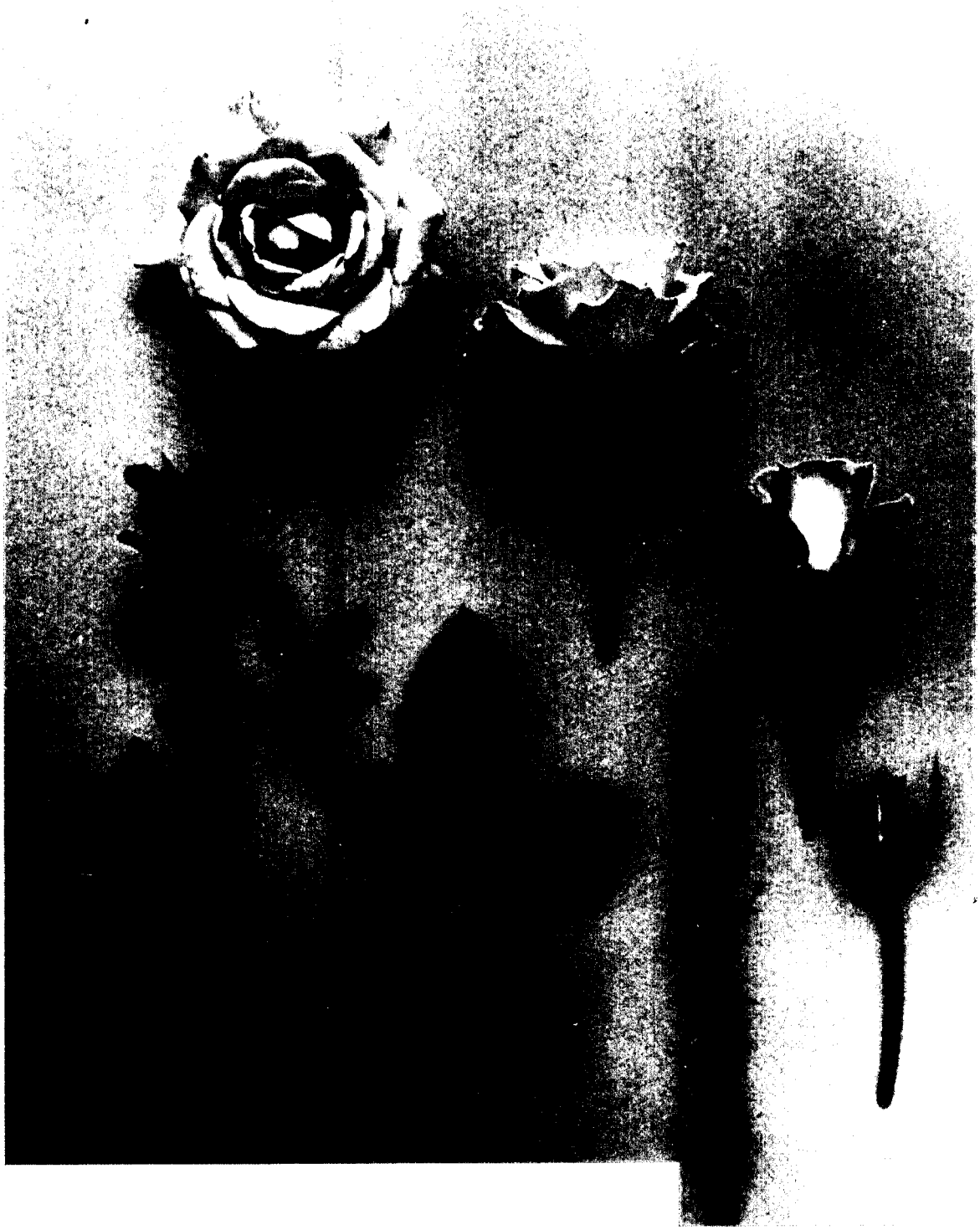

* * * * *